US006809198B2

(12) United States Patent
El Kabbani et al.

(10) Patent No.: US 6,809,198 B2
(45) Date of Patent: Oct. 26, 2004

(54) SUCRALOSE COMPOSITION AND PROCESS FOR ITS PREPARATION

(75) Inventors: Fiesal El Kabbani, Athens, GA (US); Amal Brohmi, Philadelphia, PA (US); Christian Heiss, Athens, GA (US); Juan Navia, Doylestown, PA (US); Steven J. Catani, Athens, GA (US)

(73) Assignee: Tate & Lyle Public Limited Company, London (GB)

( * ) Notice: Subject to any disclaimer, the term of this patent is extended or adjusted under 35 U.S.C. 154(b) by 0 days.

(21) Appl. No.: 10/632,876

(22) Filed: Aug. 1, 2003

(65) Prior Publication Data

US 2004/0024200 A1 Feb. 5, 2004

Related U.S. Application Data

(63) Continuation of application No. 09/991,123, filed on Nov. 16, 2001, now Pat. No. 6,646,121.
(60) Provisional application No. 60/249,782, filed on Nov. 17, 2000.

(51) Int. Cl.[7] ............................................... C13K 13/00
(52) U.S. Cl. ...................... 536/124; 536/1.11; 536/122; 536/123.1; 536/123.13
(58) Field of Search ............................ 536/1.11, 123.1, 536/123.13, 124

(56) References Cited

U.S. PATENT DOCUMENTS

| 4,343,934 | A | 8/1982 | Jenner et al. |
|---|---|---|---|
| 4,362,869 | A | 12/1982 | Jenner et al. |
| 4,380,476 | A | 4/1983 | Mufti et al. |
| 4,751,294 | A | 6/1988 | Jackson |
| 4,783,526 | A | 11/1988 | O'Brien et al. |
| 4,801,700 | A | 1/1989 | Tully et al. |
| 4,927,646 | A | 5/1990 | Jenner et al. |
| 4,950,746 | A | 8/1990 | Navia |
| 4,977,254 | A | 12/1990 | Homer et al. |
| 4,980,463 | A | 12/1990 | Walkup et al. |
| 5,141,860 | A | 8/1992 | Bornemann et al. |
| 5,298,611 | A | 3/1994 | Navia et al. |
| 5,470,969 | A | 11/1995 | Sankey et al. |
| 5,498,709 | A | 3/1996 | Navia et al. |
| 5,874,155 | A | 2/1999 | Gehrke et al. |
| 5,932,720 | A | 8/1999 | Sankey |

FOREIGN PATENT DOCUMENTS

| EP | 255260 A1 | 2/1988 | |
|---|---|---|---|
| GB | 2065646 A | 7/1981 | |
| GB | 2169601 A | 7/1986 | |
| GB | 2169601 * | 7/1986 | ............ C07H/5/02 |

OTHER PUBLICATIONS

International Search Report for application No. PCT/US01/43491 dated Aug. 6, 2002.

* cited by examiner

Primary Examiner—James O. Wilson
Assistant Examiner—Ganapathy Krishnan
(74) Attorney, Agent, or Firm—RatnerPrestia

(57) ABSTRACT

The present invention provides an improved form of sucralose and a process for making it.

16 Claims, 1 Drawing Sheet

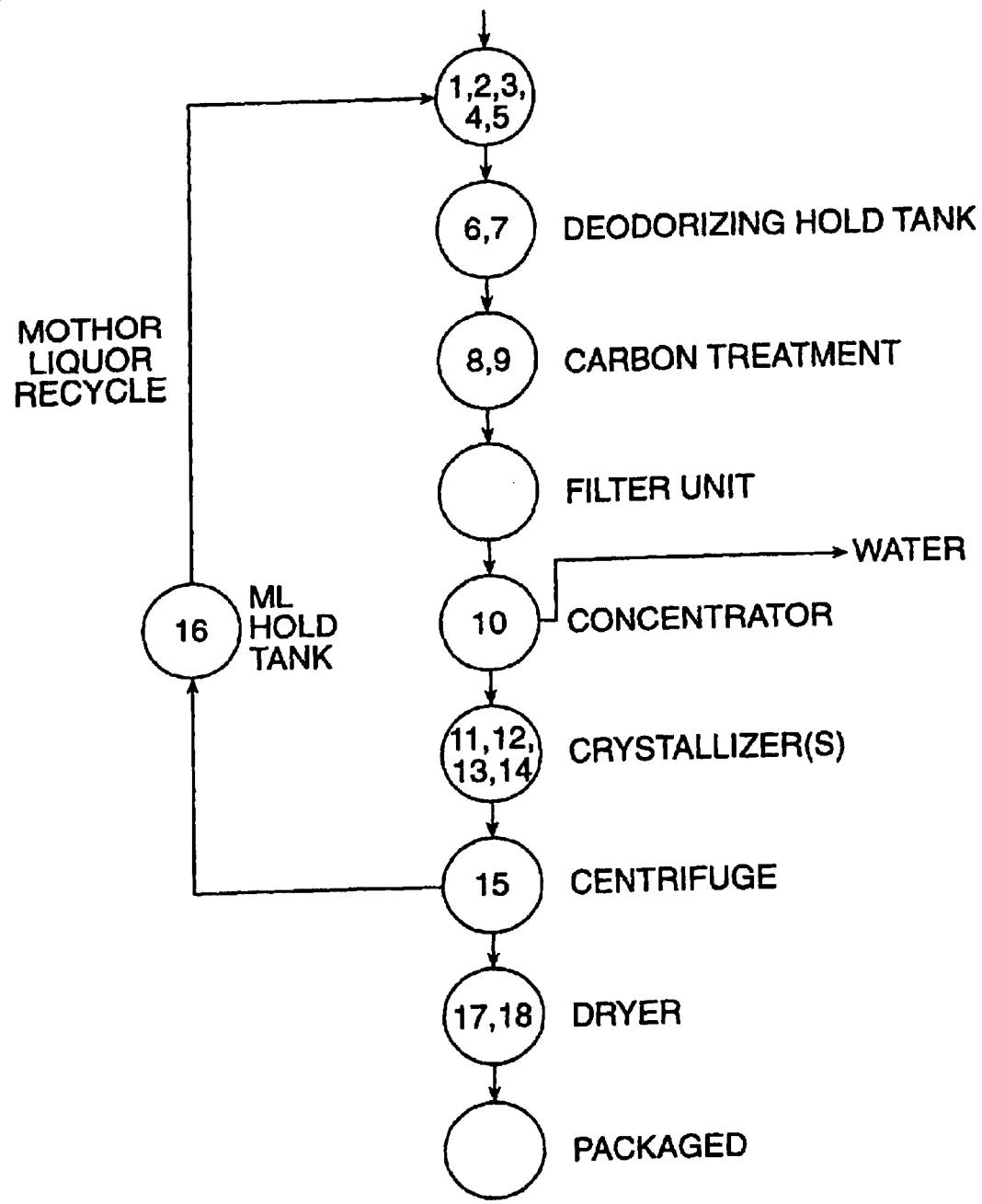

SUCRALOSE COMPOSITION AND PROCESS FOR ITS PREPARATION

This application is a continuation of U.S. patent application Ser. No. 09/991,123, filed on Nov. 16, 2001 now U.S. Pat. No. 6,646,121, which claims priority from provisional Patent Application No. 60/249,782, filed on Nov. 17, 2000. Both priority documents are incorporated herein by reference.

FIELD OF THE INVENTION

The invention relates to an improved form of sucralose and a process for making it.

BACKGROUND OF THE INVENTION

Sucralose (4,1',6'-trichloro-4,1',6'-trideoxy-galactosucrose) a high intensity sweetener made from sucrose, can be used in many food and beverage applications. Sucralose, unlike many artificial sweeteners, can be used in cooking and baking with no loss of sweetening power.

Sucralose is generally made following the procedures set forth in U.S. Pat. Nos. 4,362,869; 4,380,476; 4,801,700; 4,950,746; 5,470,969 and 5,498,709. In all these procedures one of the final steps in the synthesis is a deacylation followed by the crystallization of the sucralose. Laboratory scale methods for crystallizing sucralose have been described in U.S. Pat. Nos. 4,343,934; 5,141,860; 4,977,254; 4,783,526; 4,380,476; 5,298,611; 4,362,869; 4,801,700; and 4,980,463. As is described in many of these patents the deacylation of the sucralose precursor is performed in methanol with a catalytic amount of sodium methoxide. After completion of deacylation the resulting sucralose solution is contacted with an ion exchange resin to convert the residual sodium methoxide to methanol. The ion exchange resin is then removed and the volatile solvents and reaction byproducts are removed by co-distillation with water, which results in a solvent switch to water. The mixture is decolorized by contacting with activated carbon. The carbon is removed to provide a decolorized sucralose solution suitable for crystallizing sucralose. The sucralose solution is concentrated to about 55 weight percent sucralose (at about 50° C.). The crystallization is performed by reducing the temperature to about 22° C. and adding of about 2 percent sucralose seed crystals. The crystals that formed are separated from the mother liquor by centrifugation then dried. The mother liquor that is separated from the crystals is added to the next batch just prior to decolorization.

Unfortunately, this process has a few drawbacks. The mother liquor can become acidic over time. Additionally, the accumulation of impurities can interfere with the crystallization of sucralose, resulting in the need to periodically purge or discard the mother liquor. Crystalline sucralose, prepared as described above, generates minute amounts of hydrochloric acid, which reduces the shelf life of sucralose.

It is an object of the present invention to provide an improved process for producing a more stable form of crystalline sucralose.

It is another object of the present invention to provide an improved crystalline sucralose composition that exhibits increased stability.

SUMMARY OF THE INVENTION

We have discovered that addition of a buffer to the sucralose solution before crystallization significantly increases the stability of the sucralose crystallized from it and also increases the stability of the mother liquors during processing.

We have also discovered that by keeping the pH of the sucralose containing crystallization solution in the range of from about pH 5.5 to about pH 8.5 during the crystallization of sucralose the final stability of crystalline sucralose can be improved.

In another embodiment of the present invention, we have provided a stable crystalline sucralose product that does not develop an acetic acid odor upon storage.

In yet another embodiment of the present invention we have provided a process for the production of a stable crystalline sucralose product that does not develop an acetic acid odor upon storage.

In a further embodiment of the present invention we have also surprisingly discovered that crystalline sucralose with residual moisture content of from about 0.5 to about 10 percent by weight has improved stability.

In yet a further embodiment of the present invention we have discovered a product comprising crystalline sucralose in a container that will maintain the moisture content. Preferably the container will have moisture vapor transfer rate (MVTR) of not more than 0.25 gram water/100 square inches of surface area/24 hours, when tested at 38° C. at 92 percent relative humidity.

These inventions and other inventions will be apparent to those skilled in the art from reading the following specification (including the Examples and Claims)

BRIEF DESCRIPTION OF THE FIGURE

FIG. 1 is a flow chart of one embodiment of the crystallization process described herein. As illustrated in this embodiment an aqueous sucralose containing reaction mixture is contacted with the mother liquor and then transferred to the decolorizing tank. The mixture is then filtered and concentrated. The concentrated sucralose containing solution is transferred to a crystallizer, seeded, cooled and the crystals of sucralose are separated from the mother liquor by centrifugation. The sucralose crystals are then dried and packaged. The mother liquor is recycled to the beginning of this process.

DETAILED DESCRIPTION OF THE INVENTION

Sucralose and the methods of making sucralose have been described in numerous patents such as U.S. Pat. Nos. 4,801,700; 4,950,746; 5,470,969 and 5,498,709 which are hereby incorporated herein by reference. Following the deacylation of the protected alcohol groups in the synthesis of sucralose, the reaction mixture containing the sucralose needs to be neutralized, stabilized, decolorized and the sucralose removed from the mixture by crystallization.

The reaction mixture containing the sucralose can be neutralized by a treatment to convert any residual methoxide present to methanol. Conventionally this is accomplished by the addition of an [H+] ion exchange resin. Suitable ion exchange resins are known in the art and include AMBERLITE® IRC50 [H+] (Rohm and Haas).

To facilitate concentration and further processing of the neutralized reaction mixture any residual volatile solvents or reaction products are removed by distillation. Preferably this distillation is carried out under reduced pressure. To concentrate the neutralized reaction mixture and water is added to obtain an aqueous solution that contains from about 30 to about 70 percent by weight sucralose, preferably from about 45 to about 65 percent by weight sucralose. The reaction mixture is maintained at a temperature sufficient to keep the sucralose in solution. Generally the temperature will be from about 45° C. to about 50° C.

Before or after the neutralization of the sucralose containing solution, it may be contacted with a decolorizing agent. Most commonly the decolorizing agent will be an activated carbon, but other decolorization agents can also be used. The carbon may be in a powder form or packed in a column. However, the carbon must be removed from the solution before crystallization. The amount of carbon used will depend on the amount of colorant in the reaction mixture and the type of carbon. Those skilled in the art can readily determine the minimum appropriate amount of carbon to add to decolorize the mixture. The carbon can be removed by conventional means (e.g. by filtration) if added in a loose form.

At this point a small amount of buffer salt is added to stabilize the concentrated sucralose solution. A further adjustment to the pH is also made to provide a neutral solution. The buffer can be any food acceptable salts of food acceptable weak acids such as sodium or potassium acetate, citrate, ascorbate, benzoate, caprylate, diacetate, fumarate, gluconate, lactate, phosphate, sorbate, tartrate and mixtures thereof. Preferred buffer include sodium acetate and sodium citrate which can be used. In fact minute amounts of sodium acetate may be present as byproduct reactions insufficient to buffer the crystallization. The neutralization can be accomplished using any pH adjusting acid or base compounds that will not be inconsistent with the use of sucralose in food or compromise the taste of the final sucralose product. Generally, the following pH adjusting compounds may be used sodium, potassium, or other food acceptable salts of hydroxide, carbonate, bicarbonate acetate, citrate, ascorbate, benzoate, caprylate, diacetate, fumarate, gluconate, lactate, phosphate, sorbate, tartrate and mixtures thereof. A preferred pH-adjusting compound is sodium hydroxide.

We have however discovered that it is advantageous to use small amounts of sodium acetate such that the amount of sodium acetate in the crystallization mother liquor is maintained at a concentration of less than 100 ppm (parts per million) and preferably less than 50 ppm and most preferably from about 35 ppm to about 50 ppm to ensure that solid sucralose products do not develop an acetic acid odor.

During crystallization the pH of the sucralose containing solution should be maintained in the range of about 5.5 to about 8.5 and preferably about 6.5 to about 7.8 and most preferably about 7 to about 7.8. Maintaining the pH in these ranges significantly enhances the long-term stability of the sucralose product and the recycled mother liquors.

The sucralose may be crystallized from the sucralose containing solution using conventional crystallization equipment. The aqueous sucralose solution is concentrated to about 55 percent by weight sucralose content the sucralose and is cooled to between about 10° C. to about 30° C. and preferably between about 20° C. to about 25° C. Preferably to induce crystal formation the aqueous sucralose solution is seeded with sucralose seed. As a general guideline, seed crystals comprising about 2 percent by weight of the sucralose in the crystallization mixture appear to provide desirable crystal formation.

The crystals are separated from the mother liquor using a centrifuge or filter and the mother liquor is recycled to an earlier point in the process after neutralization and before crystallization. Preferably the mother liquor will be recycled and added to the reaction mixture after neutralization and before the decolorizing step.

The crystals may be washed to remove any residual mother liquor and dried using conventional drying equipment such as a tray or compartment dryer, agitated tray vertical turbo dyer, agitated batch rotary dryer, fluidized bed dryer or pneumatic conveying dryer. The dryer can be operated at atmospheric pressure or reduced pressure in batch or continuous modes. Experiments have unexpectedly demonstrated that sucralose stability is enhanced if the residual sucralose moisture content is in the range of about 0.5 to about 10 percent by weight and preferably from about 0.5 to about 5 percent by weight and most preferably from about 0.5 to about 2 weight percent. The sucralose referred to in this paragraph is non-hydrous meaning it does not contain any significant amounts of sucralose hydrates (e.g. sucralose pentahydrate). If the sucralose is dried to a lower moisture content the sucralose is actually less stable. The temperature in the dryer should be held below 60° C. and preferably in the range of about 35° C. to about 45° C.

Ideally the moisture content of the final sucralose product will be maintained during shipping and handling between about 0.5 to about 10 percent by weight using a package that maintains the moisture content. The less permeable the material is the more moisture will be retained and the more stable the product will be. Generally the packaging will be a container that will maintain the moisture content of the sucralose. It is desired that the container have a moisture vapor transfer rate (MVTR) of not more than 0.25 gram water/100 square inches of surface area/24 hours, when tested at 38° C. at 92 percent relative humidity. Preferably the MVRR of the container will be not more than 0.2 grams/100 square inches/24 hours. More preferably the MVTR of the container will be not more than 0.15 grams/100 square inches/24 hours. Most preferably the MVTR of the container will be not more than 0.1 grams/100 square inches/24 hours. The packaging can be flexible or rigid packaging. Suitable materials for making sucralose packaging include but are not limited to moisture limiting packaging such as metallized or aluminum foil laminated substrates such as a polymer films or a kraft paper. Suitable polymers include but are not limited to polyolefins (such as high-density (linear) polyethylene, polypropylene, etc.), polyesters (such as polyalkyl terephthalates e.g. polyethylene terephthalate, polycyclohexane-1,4-dimethylene terephthalate, polybutylene terephthalate, etc.), polyvinyl chloride, polyvinyl fluoride, and copolymers of polyvinyl chloride and polyvinyl fluoride. Additionally, packaging materials that can be used including but not limited to multi-walled paper bags having a suitable moisture barrier, fiber drums having polymeric or aluminum foil linings integral with the drum wall or loose liners inserts. Rigid containers such as blow molded drums and pails made of polymers with moisture barriers may also be used. Flexible packages such as shipping bags made of a polymer substrate are preferred. Most preferred are bags made from aluminum foil laminated to polymer films formed from polymers that are commonly used to make moisture resistant packaging (e.g. laminates of aluminum foil and the polyolefins or polyesters listed above).

EXAMPLES

General Procedures

Preparing Samples for Accelerated Stability Testing:

Label seven 6 oz. and seven 18 oz. WHIRLPAK® polyethylene bags with indelible marker for each batch being tested for stability. Accurately weigh 25 g±0.01 g of sucralose into each 6 oz. WHIRLPAK® polyethylene bag. Heat or impulse seal the 6 oz. bag to ensure air tightness. Cut off any excess polyethylene at the top of bag above the seal. Place the 6 oz. sealed bag into the 18 oz. bag and heat or impulse seal the 18 oz. bag to ensure air tightness. Roll down the top of the 18 oz. bag above the seal and bend the metal ties to form hooks.

Accelerated Stability Test:

Place the prepared bags into an oven stabilized at 50° C. ±0.5° C. by hanging them from racks by the bag hooks. The bags must be freely suspended and not touch anything. Record the time samples are placed into oven.

pH Stability:

The pH stability test is conducted on the sucralose at time zero (the day the samples are placed in the oven, before the sucralose is exposed to elevated temperature) and every 24 hours until the batch being tested fails the test.

Preparation of pH Adjusted Water:

Place approximately 100 ml of deionized water into a 150 ml beaker. Using 0.1 N hydrochloric acid and/or 0.1 N sodium hydroxide, adjust the pH of the water to be between 5.8 and 6.0. Record the pH reading.

Preparation of the Sucralose Sample Solution:

Accurately weigh 5 g±0.001 g of the product to be tested and transfer it to a 50 ml volumetric flask. Dissolve and bring to the mark by adding pH-adjusted water. If the sample to be tested is one that has been exposed to heat, remove one bag of the batch being tested from the oven and allow it to cool to room temperature before opening and sampling.

Measure the pH:

Pour the solution into a 100 ml beaker containing a stir bar, and slowly stir the solution on a magnetic stirrer. Immerse the pH electrode in the sample, allow the pH reading to stabilize and record the pH reading of the sample.

If no pH drop is observed after all the bags have been tested, the experiment is void and the test must repeated with a larger number of bags.

Color Stability:

Only a single sample need be used for this test. Prepare and heat the double bag as described above. Visually inspect the contents of the single bag prepared for color stability every 24 hours. Record the number of days to first color development.

Calculations and Interpretations:

pH Stability:

Record (to one decimal place) the pH of both the pH-adjusted water used, and the sample sucralose solution. Subtract the pH of the sample solution from that of the pH adjusted water. Report the result as (−) for a pH drop and (+) for a pH gain, e.g.:

| | |
|---|---|
| pH of pH adjusted water | 6.0 |
| pH of sample | 5.7 |
| result | −0.3 |

The sample fails the test if there is a pH drop of 1.0 pH unit or more. The pH stability of the batch is defined as the number of days until the pH drop between the sample solution and that of the pH adjusted water is ≧1.0.

Color Stability:

The color stability of the batch is defined as the number of days until the first color development is observed.

Example 1

Effect of Buffer Concentration in the Crystallization Mother Liquor on Product Stability A number of batches of sucralose were prepared with varying amounts of sodium acetate in the mother liquor and tested as above.

RESULTS:

| Sample Number | Sodium Acetate (ppm) in the Mother Liquor | Initial pH | Initial pH difference | Days to pH Failure |
|---|---|---|---|---|
| 1 | >300 | 5.72 | −0.20 | 6 |
| 2 | >300 | 5.73 | −0.19 | 6 |
| 3 | >300 | 5.44 | −0.48 | 6 |
| 4 | >300 | 5.64 | −0.28 | 6 |
| 5 | >300 | 5.64 | −0.28 | 6 |
| 6 | >300 | 5.53 | −0.39 | 4 |
| 7 | >300 | 5.70 | −0.22 | 5 |
| 8 | >300 | 5.19 | −0.73 | 5 |
| 9 | >300 | 6.19 | +0.23 | 7 |
| 10 | >300 | 5.90 | −0.05 | 5 |
| 11 | >300 | 6.05 | +0.10 | 6 |
| 12 | >300 | 5.85 | −0.10 | 6 |
| 13 | >300 | 5.85 | −0.10 | 5 |
| 14 | 35–50 | 5.95 | +0.02 | 6 |
| 15 | 35–50 | 6.06 | +0.13 | 5 |
| 16 | 35–50 | 6.20 | +0.27 | 6 |
| 17 | 35–50 | 6.03 | +0.10 | 6 |
| 18 | 35–50 | 6.00 | +0.07 | 6 |
| 19 | 35–50 | 6.06 | +0.13 | 6 |
| 20 | 35–50 | 6.09 | +0.08 | 6 |
| 21 | 35–50 | 6.05 | +0.10 | 6 |
| 22 | 35–50 | 6.08 | +0.09 | 6 |
| 23 | 35–50 | 6.12 | +0.13 | 5 |
| 24 | 35–50 | 6.02 | +0.03 | 5 |
| 25 | 35–50 | 6.03 | +0.05 | 6 |
| 26 | 35–50 | 6.06 | +0.10 | 6 |
| 27 | 35–50 | 5.99 | +0.03 | 6 |
| 28 | 35–50 | 6.00 | +0.02 | 6 |
| 29 | 35–50 | 6.09 | +0.12 | 6 |
| 30 | 35–50 | 5.95 | −0.02 | 5 |
| 31 | 35–50 | 6.03 | +0.06 | 5 |

From the tabulated data it can be seen that the average pH stability (in days to failure) of the products crystallized from a solution containing >300 ppm sodium acetate is 5.6 days. The average initial pH of those sample solutions was 5.7, and the average pH difference between the sample solution and the pH-adjusted water at time zero was −0.21 (pH drop). Several batches exhibited a mild to strong odor of acetic acid.

For those batches crystallized from a solution containing only 30 to 50 ppm of sodium acetate, the number of days to failure was the same (average of 5.7 days). The average initial pH was 6.0., while the average pH difference at time zero was +0.08. None of those batches had any acetic acid odor.

Conclusions:

The optimum level of sodium acetate in solution during the crystallization of sucralose is 35–50 ppm. This level proved to be sufficient to maintain the pH during the crystallization at acceptable levels. The stability of the final product was excellent and there was no acetic acid odor in the product.

Example 2

Effect on pH During Crystallization on Product Stability

Regardless of the amount of acetate or other buffer substance present in the crystallization, the pH of the mother liquor has a tendency to drop over time. Historically, the pH has ranged from about 3 to about 4. We have now found that if the pH is adjusted to near neutral during crystallization, the stability of the final product is significantly enhanced.

The following table records the stability results of several batches where the pH during crystallization was varied.

| Sample Number | pH at Crystallizer | Initial pH difference | Days to pH Failure |
|---|---|---|---|
| 32 | 2.75 | −0.90 | 3 |
| 33 | 2.97 | −0.94 | 4 |
| 34 | 2.97 | −1.03 | 3 |
| 35 | 6.28 | +0.10 | 5 |
| 36 | 5.99 | +0.04 | 5 |
| 37 | 5.99 | −0.06 | 5 |
| 38 | 6.07 | +0.17 | 6 |
| 39 | 6.07 | −0.02 | 7 |
| 40 | 7.01 | +0.40 | 7 |
| 41 | 6.13 | +0.40 | 5 |
| 42 | 6.34 | +0.17 | 5 |
| 43 | 6.13 | +0.29 | 5 |
| 44 | 7.11 | −0.18 | 6 |
| 45 | 7.17 | +0.17 | 7 |
| 46 | 8.05 | +0.43 | 7 |

It is evident from the data that controlling the pH at near neutrality (from about 6 to about 8) significantly increases the average stability under accelerated stability test conditions.

Example 3

Effect of Residual Moisture on the Stability of Sucralose

For several batches of sucralose, samples for accelerated stability testing were removed at intermediate moisture levels during the drying process, and the test was performed on the partially dried product as well as the final dried product. Moisture levels were determined by the loss-on-drying (LOD) procedure. The results are tabulated in the table below.

| Sample Number | Initial Moisture Content (%) | Days to pH Failure | Final Product Moisture Content (%) | Days to pH Failure |
|---|---|---|---|---|
| 35 | 2.04 | 7 | 0.05 | 5 |
| 36 | 1.87 | 7 | 0.02 | 5 |
| 37 | 8.71 | 21 | 0.02 | 5 |
| 38 | 8.07 | 23 | 0.83 | 6 |
| 39 | 4.55 | 13 | 2.00 | 7 |
| 40 | 4.01 | 13 | 1.59 | 7 |
| 41 | 3.43 | 12 | 0.08 | 5 |
| 42 | 3.16 | 9 | 0.05 | 5 |
| 43 | 5.00 | 8 | 0.02 | 5 |

These results clearly show that dry product stability is proportional to residual moisture content. This was an unexpected result, since most crystalline products are much more stable when dry.

Summary

While the residual moisture level exhibits the largest influence upon product stability, it is by no means the only important variable. It cannot overcome the effect of lack of pH control during crystallization, for example. This was demonstrated by the fact that experimental samples 32, 33 and 34, crystallized with no pH control, were actually less stable at intermediate moisture contents (3 to 5%) than they were at their final moisture levels (0.05, 0.11 and 0.21%, respectively)

Example 4

Use of Moisture Impermeable Containers for Sucralose Storage

Samples of sucralose were tested for stability using the above procedures, but using bags of different moisture permeability. All other experimental details were the same. The TYVEK®/polyethylene bags are permeable, whilst the WHIRLPAK® bags are less permeability. The A8080 bags consist of a aluminum foil laminated to low density polyethylene, which makes it very impermeable to moisture. The results are recorded below.

| Sample # | PACKAGE MATERIAL | MATERIAL PROPERTY | INITIAL MOISTURE | pH STABILITY |
|---|---|---|---|---|
| 24 | FF 91 TYVEK ®/ Polyethylene | Very permeable | 0.05% | 4 days |
| 24 | WHIRLPAK ® Polyethylene | Moderately permeable | 0.05% | 5 days |
| 24 | A8080 | Impermeable | 0.05% | 8 days |
| 47 | FF 91 TYVEK ®/ Polyethylene | Very permeable | 0.24% | 4 days |
| 47 | A8080 | Impermeable | 0.24% | 33 days |

Conclusion

By using impermeable packaging capable of retaining the moisture in the bag we were able to increase the stability of sucralose from 4 days to 33 days in accelerated stability testing. There is a direct correlation between the bag moisture permeability and product stability. It is clear that other moisture impermeable materials may be used to package sucralose and achieve this improved stability.

What is claimed is:

1. A process for the crystallization of sucralose from an aqueous solution comprising controlling the pH of said aqueous solution so as to maintain the pH in the range of from about 5.5 to about 8.5 during the formation of sucralose crystals.

2. The process of claim 1 wherein a buffer is added to the aqueous solution containing sucralose.

3. The process of claim 2 wherein the buffer is the food acceptable salt of a weak acid.

4. The process of claim 3 wherein the cation of the salt is selected from the group consisting of sodium, potassium and mixtures thereof.

5. The process of claim 4 wherein the anion of the salt is selected from the group consisting of acetate, citrate, ascorbate, benzoate, caprylate, diacetate, fumarate, gluconate, lactate, phosphate, sorbate, tartrate and mixtures thereof.

6. The process of claim 3 where the buffer is sodium acetate.

7. The process of claim 2 wherein the aqueous solution contains less than 100 ppm of buffer.

8. The process of claim 2 wherein the aqueous solution contains less than 50 ppm sodium acetate.

9. The process of claim 1 wherein the aqueous solution contains in the range of from about 35 ppm to about 50 ppm sodium acetate.

10. The process of claim 1 wherein during the recrystallization the sucralose solution is seeded with crystalline sucralose.

11. The process of claim 1 wherein the pH of the solution is in the range of from about pH 6.5 to about pH 7.8.

12. The process of claim 1 wherein the pH of the solution is in the range of from about pH 7 to about pH 7.8.

13. A process for the crystallization of sucralose comprising:
(a) adjusting the pH of a sucralose containing solution to a pH of from about 5.5 pH to about 8.5 pH; then
(b) crystallizing sucralose crystals from the sucralose containing solution thereby providing sucralose crystals and a mother liquor;
(c) separating the sucralose crystals from the mother liquor; and
(d) drying the sucralose crystals.

14. The process of claim 13 wherein the sucralose is dried to a moisture content of from about 0.5 to about 10 percent by weight.

15. The process of claim 13 wherein the sucralose containing solution is seeded with crystalline sucralose prior to crystallization.

16. The process of claim 13 wherein the pH of the sucralose containing solution is adjusted to a pH in the range of from about pH 6.5 to about pH 7.8.

* * * * *